(12) United States Patent
Barholm-Hansen

(10) Patent No.: US 6,675,821 B2
(45) Date of Patent: Jan. 13, 2004

(54) METHOD OF CONTROLLING THE FLOW IN A FLOW SYSTEM

(75) Inventor: Claus Barholm-Hansen, Vaerlose (DK)

(73) Assignee: Scandinavian Micro Biodevices A/S, Lyngby (DK)

( * ) Notice: Subject to any disclaimer, the term of this patent is extended or adjusted under 35 U.S.C. 154(b) by 0 days.

(21) Appl. No.: 10/204,177

(22) PCT Filed: Feb. 13, 2001

(86) PCT No.: PCT/DK01/00096

§ 371 (c)(1),
(2), (4) Date: Oct. 21, 2002

(87) PCT Pub. No.: WO01/61314

PCT Pub. Date: Aug. 23, 2001

(65) Prior Publication Data

US 2003/0140976 A1 Jul. 31, 2003

(30) Foreign Application Priority Data

Feb. 16, 2000 (DK) .................................. 2000 00240

(51) Int. Cl.$^7$ ................................................ F15C 1/08
(52) U.S. Cl. ................. 137/13; 137/565.33; 137/807; 137/827; 204/452; 204/601; 204/602; 204/604
(58) Field of Search ................................ 204/602, 604, 204/452, 601; 137/565.33, 807, 827, 13

(56) References Cited

U.S. PATENT DOCUMENTS

| 3,827,555 | A | * | 8/1974 | Kamentsky et al. | ........ 209/546 |
| 4,756,427 | A | * | 7/1988 | Gohde et al. | ............ 209/3.1 |
| 4,908,112 | A | * | 3/1990 | Pace | |
| 5,126,022 | A | * | 6/1992 | Soane et al. | ........... 204/458 |
| 5,429,734 | A | * | 7/1995 | Gajar et al. | ............ 204/603 |
| 5,529,679 | A | * | 6/1996 | Takahashi et al. | ......... 204/603 |
| 5,837,200 | A | | 11/1998 | Diessel et al. | |
| 5,858,187 | A | | 1/1999 | Ramsey et al. | |
| 5,858,195 | A | | 1/1999 | Ramsey | |
| 5,965,001 | A | | 10/1999 | Chow et al. | |
| 6,120,666 | A | | 9/2000 | Jacobson et al. | |

FOREIGN PATENT DOCUMENTS

WO    WO 9966318    12/1999

* cited by examiner

*Primary Examiner*—A. Michael Chambers
(74) *Attorney, Agent, or Firm*—Kilpatrick Stockton LLP

(57) ABSTRACT

With a method of controlling the flow in a flow system where a liquid flow contains a particle concentration, the liquid flow is surrounded by a carrier liquid. The liquid flow and carrier liquid are led into a central channel in which there is provided an observation area (4) where measurements of the liquid flow are effected. The result of the measurements are used to lead the liquid flow into one of several channels, in that control liquids are introduced into the liquid flow before this reaches the channels, the control liquids being derived from a capillary pump structure which pumps on the basis of an electro-kinetic effect, e.g. an electro-osmotic effect. In a preferred embodiment, the pump structure consists of two capillary structures, to each of which an electrical field can be applied. Depending on the strength of the field, the amount of control liquid will be able to be controlled so that the liquid flow with the particle concentration can be led to one of two channels. In a second embodiment, the pump structure consists of one capillary structure. The liquids can with advantage be controlled in such a manner that when the amount of liquid in the one capillary structure is increased, the amount of liquid in the second capillary structure will thus be reduced correspondingly. The advantage of the invention is first and foremost that the pumping is carried out without the use of mechanical pumping arrangements, which are relatively expensive. Moreover, a better retention of the flow pattern in the flow system is achieved.

8 Claims, 3 Drawing Sheets

METHOD OF CONTROLLING THE FLOW IN A FLOW SYSTEM

Figure 1:
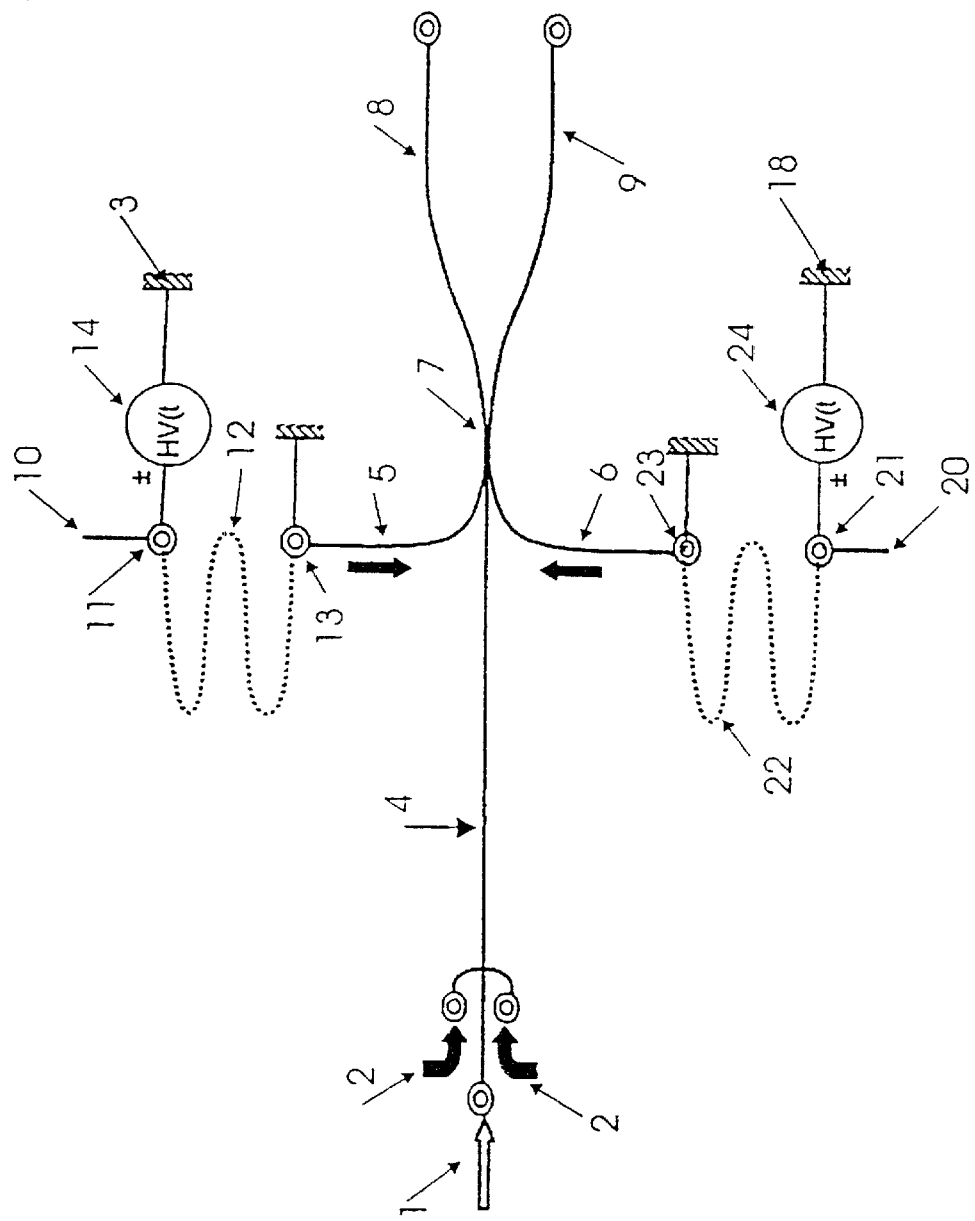

The invention concerns a method of controlling the flow of a liquid in a flow system, the liquid flow comprising particles and being led into a channel thereof, the method comprising the steps of:
- enveloping the liquid flow by a flow of carrier liquid,
- hydrodynamically focussing the particles in the liquid flow,
- providing a measurement signal of the liquid flow from an observation area in the channel, and
- dividing the liquid flow at a branching point into two or more outlets in response to said measurement signal.

The sorting of biological materials in the form of cells and microorganisms is typically carried out with a flow-cytometer, which has a sorting module.

A commonly known principle for the sorting of biological materials is brought about by first converting the liquid flow into drops, after which the drops are separated electrostatically.

With another principle, use is made of a method of separation where a volume element in a liquid flow is directed via a separate channel in relation to a main flow.

Examples of the latter principle are e.g. described in U.S. Pat. No. 3,827,555, where the separation is effected by means of mechanical valves, which are controlled on the basis of a signal from a photo-detector. However, the problem with the use of mechanical valves is that they have a relatively poor reaction time, and moreover that they unavoidably influence the flow pattern when they are activated.

In order to alleviate this problem, in U.S. Pat. No. 4,756,427 it is suggested that use be made of a piezo element which, however, is a relatively expensive component.

From WO 98/10267 a flow-switch is known where, by controlling of the part of a right and a left flow, an intermediate liquid flow can be positioned in such a manner that it can be directed through several branches at the outlets. This method is intended especially for the injection of a small liquid volume.

It is now an object of the present invention to provide a method, which results in a faster and cheaper separation of particles.

The object of the invention is achieved by a method of the type disclosed in the preamble to claim 1, which is characterised by introducing a control liquid from at least one control channel at a merging point in the channel, the amount of said control liquid being controlled by at least one electro-kinetic pump, the pump effect of which is controlled in response to said measurement signal.

In this way a system is provided where no use is made of mechanical components, which furthermore makes the system suitable for disposable set-ups, e.g. for use in so-called analysis kits.

The pump control is simple, as the pump effect varies proportionally with the applied electrical field, which is adapted to suit the given characteristics of pump liquid and the dimensions of the pump channels.

It should be noted that in addition to being able to control the central particle flow by the supply of a control liquid, a control of the central particle flow could also be achieved by the electro-kinetic pumping of liquid away from the central flow, naturally providing that this liquid permits the use of electro-kinetic pumping mechanisms. Moreover, the two control methods can be combined, hereby achieving, among other things, a greater displacement of the central particle flow.

It is expedient for the method to be executed as disclosed in claim 2, where said at least one electro-kinetic pump is of an electro-osmotic type consisting of two capillary structures to each of which an electrical field is applied, so that when the field in the one capillary structure is increased, the field in the other capillary structure is correspondingly reduced.

By a particularly simple embodiment of the method according to the invention, as disclosed in claim 4, the amount of control liquid is controlled by just one electro-kinetic pump, which is placed in the one of the channels. By introducing control liquid in greater or smaller degrees, or by pumping liquid away from the channel, the central particle flow can be controlled between the two outlets. The configurations with differences in the channel cross-section, as well as asymmetrical configurations of the branching point, will be able to be used in connection with the controlling of the central particle flow.

Besides, other advantageous configurations of the invention are disclosed in the dependent claims.

Figure 2:
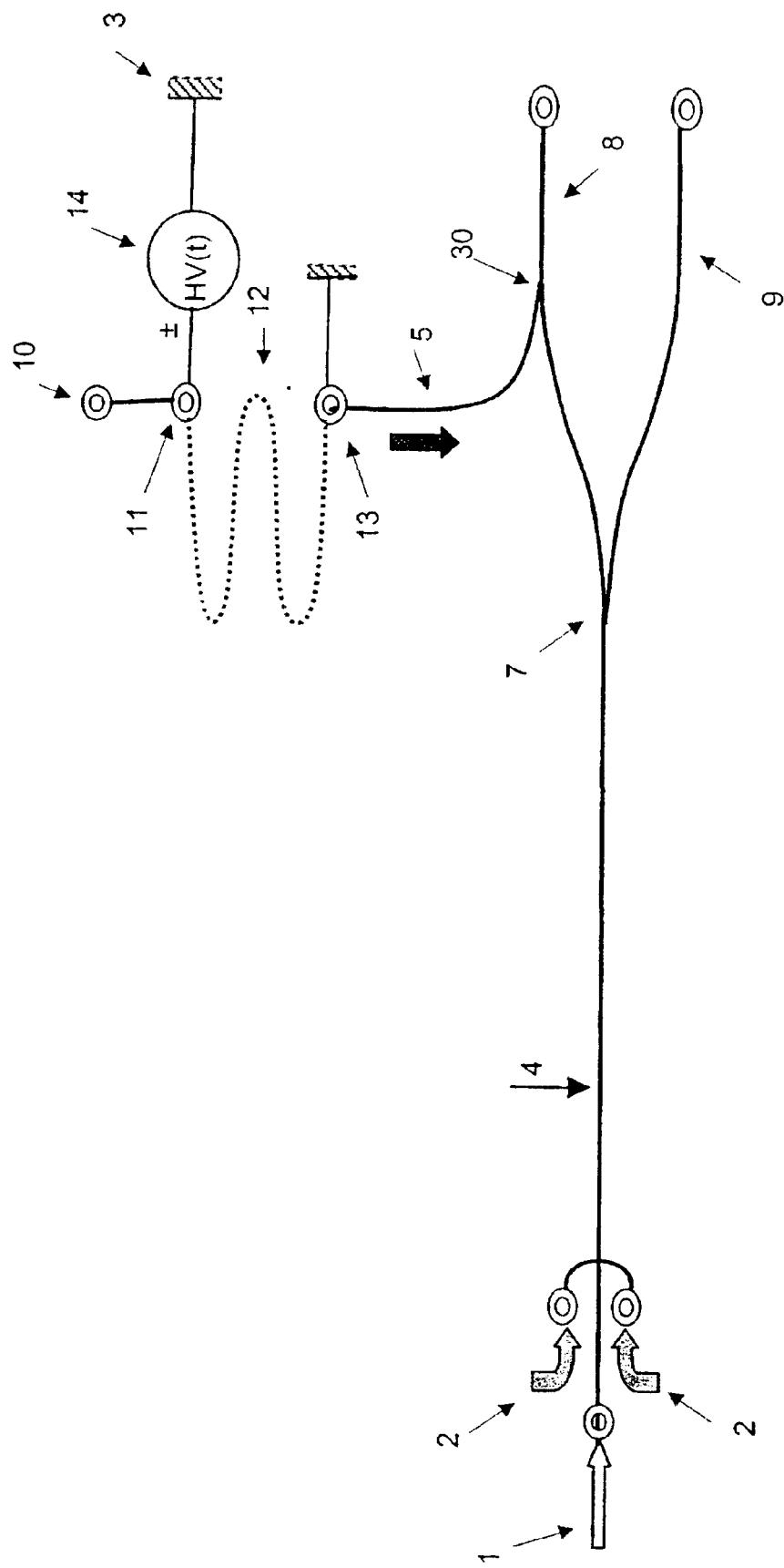
Figure 3:
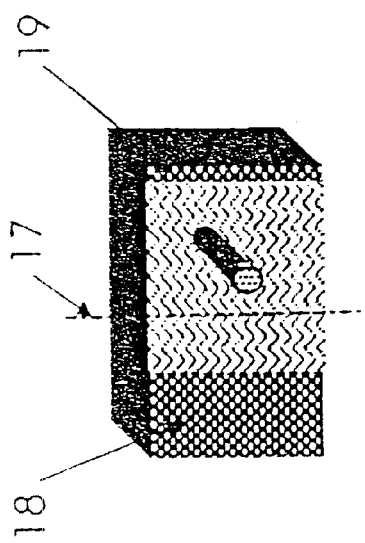
Figure 3:
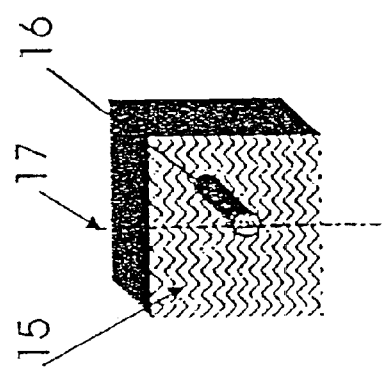
Figure 3:
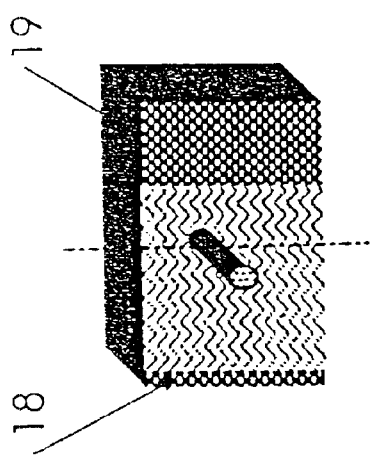

The invention will now be explained in more detail with reference to the example embodiment shown in the drawing, where FIG. 1 shows a principle set-up of the flow system in a first embodiment according to the invention, FIG. 2 shows a principle set-up of the flow system in a second embodiment according to the invention, while FIG. 3 shows the principle involved in how a volume element can be controlled by use of electro-kinetic pumps according to the embodiment in FIG. 1.

In FIG. 1 the reference FIG. 1 indicates a liquid flow containing particles, which liquid flow is led into a central channel. The liquid flow is enveloped in a "carrier flow" 2 in the central channel, so that hydrodynamic focussing occurs, whereby the particles assume a very uniform movement pattern in the central channel.

At a suitable distance inside the channel an observation area 4 is arranged. In this area, the particles pass in an individual manner due to their so-called "focussing". Not-shown measuring equipment can be established in the observation area for providing measurements, which form the basis for the further passage of the particles through the system, cf. below.

After the observation area 4, the particles move further through the central channel and reach a merging area where control liquids are led into the central channel from two connected channels 5 and 6. After the merging area, the channel is divided into two further channels 8 and 9.

It takes the particles a known time, τ, to move from 4 to 7. Within this period of time, τ, the control signals, which control the control liquids, are generated. The time, τ, is determined by the length of the channel and the rate of flow in this channel.

The particles from the liquid flow will now be introduced into the channels 8 or 9, depending on how much control liquid is introduced into the channels 5 and 6 from two reservoirs 10 and 20.

It should be noted that the control liquids could be other than the particle-containing liquid and the carrier flow, which provides degrees of freedom in optimising the electro-kinetic pumping.

The control liquid from the reservoirs 10 and 20 is pumped by means of a pump structure, which is based on an electro-kinetic effect, e.g. electro-osmosis.

In FIG. 1 the pump structure is shown as a capillary structure 12 between the reference FIGS. 11 and 13. The drawing shows identical structures on each side of the central channel and branching point 7, in that the additional structure is indicated by the reference FIGS. 22, 21 and 23, respectively.

With an electrical field applied over a part of the capillary structures between supply pieces 11 and 13 and 21 and 23, liquid is pumped from the reservoirs 10 and 20 in towards the central particle flow.

As will appear from FIG. 1, the merging area is electrically earthed at 13 and at 23, respectively. The whole of the channel system is hereby held at a safe potential, and the relatively high potential, which is required for pumping, can be limited to the structures between 13 to 10 and 23 to 20, respectively.

The amount of liquid, which is pumped through the capillary structures, is controlled by changing the magnitude of the applied electrical field, which can be modulated temporally. A typical field strength is of 200 volts/cm, and the overall potential measured between 10 and 23 can be up to several kilovolts.

The high voltage supplies 14 and 24 are connected to electrical earth at 3 and 18, respectively.

In a typical set-up, a constant total amount of control liquid is pumped through the two capillary structures. It is hereby avoided that the pressure conditions around the introduction of the enveloped liquid flow are influenced by the sorting function. In other words, an increase/reduction of the amount of liquid in the one channel will result in a corresponding reduction/increase of the amount of liquid in the other channel.

With many applications, the ratio between the control liquids can with advantage be arranged so that a changeover of the control liquids in the ratio of 20:80 can be brought about.

This means, for example, that when a field is applied in the upper capillary structure which corresponds to 20% of the total control liquid from the one reservoir 10 being supplied to the upper capillary structure, in the lower capillary structure the remaining 80% will thus be pumped from the second reservoir 20 and vice versa.

FIG. 2 shows a second embodiment in which an electro-kinetic pump is connected after the branching point 7. In this embodiment, only one pump is shown, which is sufficient to give rise to a change in the flow pattern. When the flow in the channel 8 is increased with a contribution via the merging point 30, a greater part of the main flow will be forced over into the other channel 9. The central particle flow will hereby be changed over from channel 8 to channel 9.

Here it should be noted that if a pump effect is not initiated from the electro-kinetic pump, the particles will then flow in the channel 8, which is due to the adjustment of the hydrodynamic focussing in the central channel, so that the particles move along the one side of the central channel, which in the drawing is shown at the observation area with the reference FIG. 4.

The pump structures can alternatively be realised as external components, which e.g. are connected to the remaining flow system via an HPLC hose, or by part components being integrated on a common substrate.

In FIG. 3, the reference FIG. 15 indicates a volume element of the central liquid flow with hydrodynamically focussed particles at 16 in the observation area 4 in FIG. 1.

As will be seen, the focussed particles lie symmetrically around the axis 17.

After the introduction of control liquid from each of the channels 5 and 6, lowermost in FIG. 3 it is shown how control liquid from the channels 5 and 6 can displace the focussed particles to the right or left in the branching point 7.

To the left in FIG. 3, the ratio between control liquids in the channels 5,6 is thus shown as being 20:80, cf. reference FIGS. 18 and 19, and on the right-hand side as 80:20. In the two cases, the focussed particles will be led to the channels 8 and 9, respectively.

Moreover, it should be noted that by increasing the length of the capillary pump structure, a higher hydrostatic pressure is achieved at unchanged diameter of the capillary structure and with no change in the applied electrical field.

With retained length and retained electrical field, the flow will be increased with the cross-sectional area of the pump channel, while at the same time a higher electrical current will flow.

The structure can be made of glass or of polymer material or of another suitable composition of materials, which are known within the field of micro-mechanics.

The channels can possibly be surface treated or coated with a thin film, e.g. in order to improve the electro-kinetic pumping.

It should be noted that special constructions would find application around the focussing zone and the detection point 4.

In general, the electro-kinetic pumps, which are described in connection with the said structures, will be able to be replaced by other pump mechanisms, though with subsequent modification of the system's parameters.

What is claimed is:

1. A method of controlling the flow of a liquid in a flow system, the liquid flow comprising particles and being led into a channel thereof, the method comprising the steps of:
    enveloping the liquid flow by a flow of carrier liquid (2),
    hydrodynamically focussing the particles in the liquid flow,
    providing a measurement signal of the liquid flow from an observation area (4) in the channel, and
    dividing the liquid flow at a branching point (7) into two or more outlets in response to said measurement signal, wherein said division of the liquid flow comprises:
        introducing a control liquid from at least one control channel (5,6) at a merging point (30) in the channel, the amount of said control liquid being controlled by at least one electro-kinetic pump, the pump effect of which is controlled in response to said measurement signal.

2. The method according to claim 1, wherein said at least one electro-kinetic pump is of an electro-osmotic type consisting of two capillary structures to each of which an electrical field is applied, so that when the field in the one capillary structure is increased, the field in the other capillary structure is correspondingly reduced.

3. A method according to claim 2, wherein the electrical fields are controlled, e.g. in the ratio of 1:5, to bring about a liquid flow from the central channel in such a manner that the particles in the liquid flow are controlled in dependence of the fields.

4. A method according to claim 1, wherein the amount of control liquid is controlled by just one electro-kinetic pump, which is placed in the one of the channels (5,6).

5. A method according to claim 1, wherein the flow is divided in two or more outlets after the branching point, whereby the particles are sorted in accordance with their position at the branching point.

6. A method according to claim 2, wherein the capillary structures have a cross-section, which varies between 0.00005 mm$^2$ and 1.00000 mm$^2$.

7. A method according to claim 1, wherein said pump effect is controlled on the basis of measurement signals which are generated in an observation area which lies up-stream said merging point for said control liquids.

8. A method according to claim 1, wherein the flow system is configured in a monolithic manner with integrated pumps or by connection of separate pumps.

\* \* \* \* \*